(12) United States Patent
Pariente et al.

(10) Patent No.: US 9,315,440 B2
(45) Date of Patent: Apr. 19, 2016

(54) PROCESS FOR OBTAINING ACROLEIN BY CATALYTIC DEHYDRATION OF GLYCEROL OR GLYCERIN

(75) Inventors: Stephane Pariente, Bagnolet (FR); Virginie Belliere-Baca, Andresy (FR); Sebastien Paul, Thun Saint-amand (FR); Nouria Fatah, Vendeville (FR)

(73) Assignees: ADISSEO FRANCE S.A.S., Antony (FR); ECOLE CENTRALE DE LILLE, Villeneuve D'Ascq (FR)

( * ) Notice: Subject to any disclaimer, the term of this patent is extended or adjusted under 35 U.S.C. 154(b) by 31 days.

(21) Appl. No.: 13/881,877

(22) PCT Filed: Oct. 26, 2011

(86) PCT No.: PCT/FR2011/052492
§ 371 (c)(1),
(2), (4) Date: Apr. 26, 2013

(87) PCT Pub. No.: WO2012/056166
PCT Pub. Date: May 3, 2012

(65) Prior Publication Data
US 2013/0217909 A1 Aug. 22, 2013

(30) Foreign Application Priority Data
Oct. 26, 2010 (FR) ..................... 10 58767

(51) Int. Cl.
| C07C 45/52 | (2006.01) |
| C07C 317/14 | (2006.01) |
| C07C 319/18 | (2006.01) |
| C07C 319/20 | (2006.01) |
| C07C 319/14 | (2006.01) |

(52) U.S. Cl.
CPC .............. *C07C 45/52* (2013.01); *C07C 319/14* (2013.01); *C07C 319/18* (2013.01); *C07C 319/20* (2013.01); *Y02P 20/584* (2015.11)

(58) Field of Classification Search
None
See application file for complete search history.

(56) References Cited

U.S. PATENT DOCUMENTS

| 7,119,233 B2 * | 10/2006 | Dubner et al. ................. 568/63 |
| 2011/0028760 A1 | 2/2011 | Dubois et al. |
| 2011/0152582 A1 * | 6/2011 | Strohm et al. ................ 568/857 |
| 2011/0184191 A1 | 7/2011 | Menendez Sastre et al. |
| 2011/0229626 A1 | 9/2011 | Devaux et al. |

FOREIGN PATENT DOCUMENTS

| JP | 2010155183 A | | 7/2010 |
| WO | WO2006/087084 | * | 8/2006 |
| WO | 2009153382 A1 | | 12/2009 |

* cited by examiner

*Primary Examiner* — Rebecca Anderson
*Assistant Examiner* — Po-Chih Chen
(74) *Attorney, Agent, or Firm* — Porzio, Bromberg & Newman, P.C.

(57) ABSTRACT

A continuous process for obtaining acrolein by catalytic dehydration of glycerol or glycerin, in the presence of an acid catalyst, wherein said process comprises the concomitant regeneration of said catalyst and is carried out in a fluidized bed reactor, said reactor comprising two zones, a first zone, or lower zone, termed catalyst regeneration zone, in which a fluidization gas comprising oxygen is introduced, and a second zone, or upper zone, termed reaction zone, in which the glycerol or glycerin is introduced and converted into acrolein.

11 Claims, 4 Drawing Sheets

PROCESS FOR OBTAINING ACROLEIN BY CATALYTIC DEHYDRATION OF GLYCEROL OR GLYCERIN

CROSS REFERENCE TO RELATED APPLICATION

This is a National Stage of International Application No. PCT/FR2011/052492, filed 26 Oct. 2011, which claims the benefit of Application No. 10/58767, filed in France on 26 Oct. 2010, the disclosures of which Applications are incorporated by reference herein.

The present invention relates to the catalytic production of acrolein by dehydration of glycerol or glycerin. More specifically, the invention relates to a continuous process for the production of acrolein from glycerol or glycerin, in the presence of an acid catalyst, in a fluidized bed catalytic reactor, making it possible to overcome the inadequacies of the known processes relating to the coking of the heterogeneous catalysts employed.

Acrolein, of formula $H_2C=CH-CHO$, is the simplest of the unsaturated aldehydes. It constitutes an important intermediate in the chemical and food processing industries. This is because it is a precursor for acrylic acid, which plays an important role in the manufacture of plastics and paints. However, the most important use of acrolein is the synthesis of D,L-methionine, which is an essential amino acid for animal feeding and which has no or very few natural sources. Generally, acrolein results from the selective oxidation of propylene by atmospheric oxygen over complex catalysts formed of mixed oxides of bismuth and molybdenum (see, for example. G. W. Keulks, L. D. Krenzke and T. M. Notermann, Adv. Catal., 1978, 27, 183). The selectivity for acrolein obtained by this process is greater than 80% with a high conversion of the propylene (greater than 90%). As the latter results from the catalytic cracking of petroleum fractions, the availability thereof and the price thereof are thus dependent on those of the fossil resources.

In this context, the production of acroleins from a renewable starting material via an industrial process which is effective and stable over time is of great interest. This is why numerous studies have been carried out on the synthesis of acrolein by dehydration of glycerol (see, for example, the review by B. Katryniok, S. Paul, M. Capron and F. Dumeignil, ChemSusChem, 2009, 2, 719-730). This is because glycerol is obtained in a proportion of 100 kg per tonne of biodiesel produced by transesterification of vegetable oils. As European Directive 2003/03/30EC has set the share of the biodiesel market in fuels at 10% for 2015, the production of biodiesel has experienced very strong growth in recent years (5.7 million tonnes produced in European in 2007, a figure which should double by 2012). This increase in production is, of course, automatically accompanied by a very significant increase in the amount of glycerol available on the market.

A few examples of studies relating to the dehydration reaction of glycerol to give acrolein are presented below in order to illustrate the technological hurdles which the present invention makes it possible to overcome and thus to show the advances obtained.

It has been known for a long time that acid catalysis makes it possible to carry out the dehydration of glycerol to give acrolein. Specifically, H. Adkins and W. H. Hartung, Organic Synthesis I, 15-18 (1964), showed this possibility at 190-200° C. by virtue of a treatment of glycerol over potassium sulfate and potassium hydrogensulfate powders. The document U.S. Pat. No. 2,558,520 A relates to the dehydration of glycerol over diatomaceous earths impregnated with orthophosphoric acid to give an acrolein yield of 72.3% at 283° C. In these studies, the reaction temperature is high, which is harmful to the achievement of good selectivity for acrolein.

In the document U.S. Pat. No. 5,387,720 A, the dehydration is carried out in the gas or liquid phase in a reactor of fixed bed type. The catalysts used are acidic solids with Hammett acidities of less than +2 and preferably of less than −3. The gas phase reaction gives glycerol conversions of approximately 100% at temperatures between 250 and 340° C., with an acrolein yield of 70.5% and a hydroxypropanone yield of approximately 10%, under a reaction stream of 40 ml min$^{-1}$ of a 20% by weight aqueous glycerol solution over a period of 60 h. Other by-products are also detected during the dehydration reaction of glycerol to give acrolein, such as propanaldehyde, acetaldehyde, acetone and other compounds which result in the formation of coke on the catalyst and thus in its rapid deactivation. The life time of the catalyst is thus very low in this case.

The documents WO2007/058221A1 and JP2008-088149A describe the use of heteropolyacids grafted to silica as catalyst for the dehydration of glycerol to give acrolein. The reaction is carried out in a fixed bed reactor with a 10% by weight aqueous glycerol solution and at temperatures between 250 and 325° C. The reaction time is 5 h. A comparison is carried out between the supported heteropolyacid catalysts and the various types of acid catalysts, such as $Al_2O_3$, $SiO_2$—$Al_2O_3$, $SiO_2$, $TiO_2$, $ZrO_2$, and the like. The glycerol conversions are always approximately 100% and the best acrolein yields reach 87%. The reaction was not carried out for reaction times longer than 5 h because of the high deactivation experienced for a longer working period of the catalyst.

The document WO2009/029540A2 relates to the use of different solid supports, such as $Al_2O_3$, $ZrO_2$, $SiO_2$—$AlO_3$, $SiO_2$—$Al_2O_3$, alundum, $SiO_2$ or Ludox AS30, on which metal phosphates of formula $M_{0.33}H_{2.33}PO_4$, with M=Ba, Cr, Mn, Fe, Co, Ni, Zn, La, Ru or Mo, are impregnated. Catalysts based on Nb, tungstic acid and phosphomolybdic acid are also described in this document. The reaction is carried out in a fixed bed with aqueous solutions of glycerol at contents of between 17% and 30% by weight and at temperatures ranging from 250 to 320° C. The acrolein yields reach 87% but neither the reaction time nor the data relating to any regeneration of the catalyst are given, it being known that, at these temperatures and with these yields, the production of coke on the catalyst is inevitably high.

In order for these results, obtained with whatever catalyst, to be able to be sufficiently convincing economically and thus to result in a true industrial process, it is thus necessary to solve the problem of deposition of coke on the catalyst by limiting its formation and/or by removing it periodically or continuously.

The document JP2008-110298A tackles the subject of the regeneration of the catalyst in a fixed bed reactor with a catalyst of zeolite type. Cycles with 12 h of reaction followed by 18 h of regeneration under air are carried out in order to recover the starting activity. It is found here that the regeneration time is 1.5 times greater than the working duration of the catalyst, which represents a major brake in terms of productive output.

The document DE102008038273 A1 deals with the implementation of the dehydration of glycerol in the gas phase in two fixed bed reactors placed in parallel. This is because the process provides for the use of a first reactor up to a deactivation equivalent to a loss in activity of 10% and then for a change in reactor, in order to regenerate the coked catalyst in parallel without halting production. This efficient process is expensive since it requires the use of two reactors in parallel.

Arkema has filed numerous patent applications relating to catalytic processes for the dehydration of glycerol to give acrolein, generally coupled with a second stage of oxidation of the acrolein obtained to give acrylic acid. In particular, the document FR 2 882 052 A1 describes that the addition of molecular oxygen to the gas mixture feeding a fixed bed reactor makes it possible to prevent/limit the formation of coke and aromatic compounds, such as phenol, and also other by-products originating from a hydrogenation of dehydrated products, such as propanaldehyde and acetone but also hydroxypropanone. Under these conditions, the document WO2009/127889A1 thus indicates acrolein yields by dehydration of glycerol of the order of 93% for reaction temperatures ranging from 260 to 350° C. over catalysts of the type comprising salts of silicic or phosphoric heteropolyacids doped with various elements, such as Cs, Rb, Ca, Fe, Zr, La, Hf or Bi. The reaction is carried out in a fixed bed with a percentage of molecular oxygen in the feed of less than 7%, in order to remain outside the explosive limits for acrolein/air mixtures. No information present in this document allows conclusions to be drawn with regard to the stability over time of such systems. However, one publication (A. Alhanash, E. F. Kozhevnikova and I. V. Kozhevnikov, Applied Catalysis A: General, 378 (2010) 11-18) reports the use of catalysts identical to those tested in the document WO2009/127889A1 and a rapid loss in acrolein yield as a function of the reaction time is then observed. This is because the acrolein yield changes from 98% after one hour under the reaction stream to only approximately 40% after 6 hours under the stream. It is therefore highly probable that the trend is the same for the process which is the subject matter of the document WO2009/127889A1.

The document WO2008/052993A2 relates to the production of acrolein from glycerol in a circulating bed composed mainly of zeolite ZSM-5 and clay beads. The conversion of the glycerol, at temperatures between 290 and 500° C. and with 20%, 50% or 85% by weight aqueous glycerol solutions, is always approximately 100% but the selectivity for acrolein remains low, that is to say approximately 60%. In addition, the use of a circulating bed reactor exhibits not insignificant disadvantages for an industrial application, such as the large amount of catalyst to be employed, the difficulty of running such a unit or also the need to have available a catalyst which is sufficiently resistant to the extremely high mechanical stresses encountered in this type of reactor (attrition phenomenon).

All the processes described in the preceding references for carrying out the catalytic dehydration of glycerol to give acrolein exhibit significant limitations in terms of life time of the catalysts, which is totally unacceptable for industrial viability. The techniques disclosed to increase the life time of these catalysts (continuous decoking) result either in significant losses in acrolein productive output or in very high capital costs. Similar hurdles are encountered in other fields of application and advantageous solutions have been provided.

The document U.S. Pat. No. 3,669,877 A, published in 1972, describes the reaction for the dehydrogenation of butane over a chromium-aluminum catalyst in a fluidized bed reactor, the bottom part of which above the distributor is a simple fluidized bed and the top part of which is divided into two annular regions by virtue of the addition of a hollow cylinder to the reactor. The region thus created inside the hollow cylinder in the top part will be the reduction region. The annular part around the cylinder acts as regeneration (oxidation) region. Finally, the bottom part allows the solid to circulate between the two top regions. Feeding of the hollow cylindrical part takes place with a reducing gas and feeding of the top annular part takes place with an oxidizing gas, such as oxygen, making possible the regeneration of the catalyst.

The document U.S. Pat. No. 4,152,393 A, published in 1979, relates to the invention of an entrained bed reactor not using the technology of fluidized beds. This reactor is divided into four vertical compartments, where the solid moves from the bottom upwards or from the top downwards. The core of the reactor, which acts as regeneration region, is surrounded by three successive concentric rings. The solid is entrained by a gas from the core of the reactor according to an upward movement towards the first ring (the closest to the core of the reactor), where the particles move according to a downward stream, this ring being used to separate the reaction and regeneration gases. Subsequently, the solid is entrained into the second ring (upward movement of the solid), which constitutes the reactive part. Finally, the third ring is used to cause the solid to move back from the reactive part to the core of the reactor.

The document U.S. Pat. No. 6,197,265 B1 also reports a fluidized bed reactor, this time comprising two regions, these being created by a novel system for distributing the gas within the fluidized bed. It is a matter here of separating an oxidation region and a reduction region.

A reactor of fluidized bed type having two regions in which the density of the solid is different by virtue of different gas flow rates, with a greater reactor cross section in the densest part with the aim of preventing the entrainment of the particles, is described in the document US2007/0213573A1. This reactor is used for catalytic cracking reactions.

A process for the preparation of a vinylaromatic compound, such as styrene, from an alkylaromatic compound, such as ethylbenzene, by dehydrogenation of the latter in a reactor of fluidized bed type comprising two regions (a dehydrogenation region and a regeneration region), forms the subject matter of the document WO0144146A1. This document also reports an injection system immersed at different heights in the fluidized bed in order to bring about the separation of the two regions. In view of the fact that dehydrogenation reactions are concerned here, the catalyst will experience of a phase of coking in the top part of the reactor and the coke will be incinerated in the bottom part, which makes it possible to obtain a process exhibiting a conversion and a selectivity stable over a period of more than 200 h.

Finally, more recently, the document WO2009/153382A1 describes a fluidized bed comprising two regions, with injection of the reactant into a conical top part of the reactor for oxidation, dehydrogenation-oxidation and dehydrogenation reactions. This configuration is capable of introducing a clearer separation between the two regions.

The authors of the present invention thus propose to take as basis a technology formed of a fluidized bed reactor having a reaction region and a regeneration region in order to develop an effective and stable process for the production of acrolein from glycerol or glycerin. In contrast to the prior art set out above, the invention relates to an unpublished use of this type of reactor for a dehydration reactor.

Thus, the invention described in the present patent provides for the dehydration of glycerol to give acrolein to be carried out in a fluidized bed catalytic reactor comprising a reactive region and regenerating region in the same chamber which makes possible the continuous decoking—and thus the continuous regeneration—of the catalyst employed within the reactor. This invention thus makes it possible to continuously produce acrolein from glycerol or glycerin, while retaining the high performance over time of the acid catalysts used.

A subject matter of the invention is thus a continuous process for the production of acrolein by catalytic dehydration of glycerol or glycerin in the presence of an acid catalyst, said process comprising the concomitant regeneration of said catalyst and being carried out in a fluidized bed reactor, said reactor comprising two regions, a first region, or lower region, referred to as region for regeneration of the catalyst, into which an oxygen-comprising fluidizing gas is introduced, and a second region, or upper region, referred to as reaction region, into which the glycerol or the glycerin is introduced and converted into acrolein.

Before tackling the invention in more detail, the terms "glycerol" and "glycerin" are defined. According to the invention, glycerol is understood to mean a purified or unpurified glycerol, preferably resulting from biomass, and in particular a highly purified or partially purified glycerol. A purified glycerol has a purity of greater than or equal to 98%, obtained by distillation of glycerin. Glycerin is understood to mean in particular a glycerin of natural origin, resulting from the hydrolysis of vegetable oils or animal fats, or a glycerin of synthetic origin, resulting from petroleum, which is more or less purified or refined, or else crude. Thus, in the continuation of the description, the reference to glycerol or to glycerin applies to all glycerols and glycerins, whatever their origin, in particular natural or synthetic, and their degree of purity.

As indicated above, the reactor comprises two regions, an upper region and a lower region. Advantageously, it exhibits the following structure:

the upper region of the reactor comprises, from the bottom upwards, i) a part for introduction of the glycerol or glycerin, ii) a part for reaction by catalytic dehydration of the glycerol or glycerin, and iii) a part for release of the fine solid particles formed, and/or the lower region of the reactor comprises, from the bottom upwards, a conical part for introduction of the fluidizing gas and a region for regeneration of the catalyst by the fluidizing gas.

An optimum result is obtained when the implementation of the above process corresponds to the preferred characteristics below, considered alone or in combination:

the glycerol or the glycerin is introduced in the form of an aqueous solution in a concentration varying from 10% to 90% by weight; advantageously, said solution is introduced in the vaporized form; the injection of the reaction mixture, that is to say the glycerol or glycerin solution, can be carried out at different heights in the bed;

the dehydration temperature varies from 180 to 500° C.;

the fluidizing gas is chosen from air, $O_2$ and an $O_2/N_2$ mixture comprising up to 21 mol % of molecular oxygen; the percentage of oxygen present in the bottom part of the fluidized bed can be adjusted in order to continuously incinerate the coke formed in the top part of the bed;

the fluidizing gas is heated to a temperature varying from 180 to 800° C., preferably at a pressure varying from atmospheric pressure to 10 bar.

Another major advantage of this invention lies in the possible use of a wide range of fluidizable solid acid catalysts for the production of acrolein from glycerol or glycerin, it being possible for the operating conditions in the reactor to be adjusted to the conditions for functioning of the acid catalyst used. Thus, as nonlimiting examples, the acid catalyst can be chosen from zeolites, phosphates (such as iron phosphates), heteropolyacids, which are optionally supported and/or doped, catalysts of oxide or supported oxide types, or also of the type formed of zirconias, which are modified and/or doped, and also any other type of acid catalyst which is suitable for the dehydration of glycerol to give acrolein and which exhibits a sufficient resistance to attrition to be employed in the fluidized bed. According to one of the alternative forms of the invention, the catalyst is chosen from supported or unsupported heteropolyacids doped with at least one metal chosen from Cs, Rb, Ca, Fe, Zr, La, Hf and Bi.

The present invention makes it possible to continuously produce acrolein from glycerol or glycerin over very long periods of time. The specific properties of the fluidized beds make it possible to keep compositions highly partitioned from the gas phase in each region. The catalyst, which moves very rapidly between the two lower and upper regions, is thus subjected to ceaseless very short deactivation-regeneration cycles. It is therefore possible to adjust the operating parameters for the functioning of the fluidized bed in order to optimize the dehydration/regeneration process. In particular, the contact time between particles and gas will be controlled by the height of the fluidized bed in the reactor. The high acrolein productive output of the catalyst is maintained by adjusting the partial oxygen pressure in the fluidization gas in order for it to be completely consumed exactly at the level of the injection of the glycerol or glycerin. Thus, neither the glycerol or glycerin nor the acrolein formed are in the presence of oxygen and cannot be decomposed by oxidation, as in the case of inert material/oxygen cofeeding in a fixed bed, which has harmful effects on the selectivity. The functioning is also highly favorable from the thermal viewpoint since the heat generated by the combustion of the coke is used for the reaction for dehydration of the glycerol, which is slightly endothermic. In addition, the process described in the present invention benefits from the advantages of the fluidized bed, namely: very good gas/solid contact, promoting exchanges of material and energy between the two phases; excellent uniformity in temperature and concentration throughout the whole of the reaction volume and source of a low fall in pressure. Moreover, in a fluidized bed, the withdrawal of irreversibly deactivated catalyst and the addition of fresh catalyst can take place without halting production.

The invention also relates to a process for the manufacture from acrolein of 3-(methylthio)propionaldehyde MMP, 2-hydroxy-4-(methylthio)butyronitrile HMTBN, methionine, 2-hydroxy-4-(methylthio)butanoic acid HMTBA, esters of the latter, or 2-oxo-4-(methylthio)butanoic acid KMB, in which process the acrolein is obtained by catalytic dehydration as described above.

The further subject matter of the invention is the use, in the continuous production of acrolein by catalytic dehydration of glycerol or glycerin in the presence of an acid catalyst, of a fluidized bed reactor, said reactor corresponding to the characteristics described above in order to carry out the process of the invention.

The present invention is now set out in more detail and is illustrated with the support of the following FIGS. 1 to 4 and examples 1, 2, 3 and 4:

Figure 2:
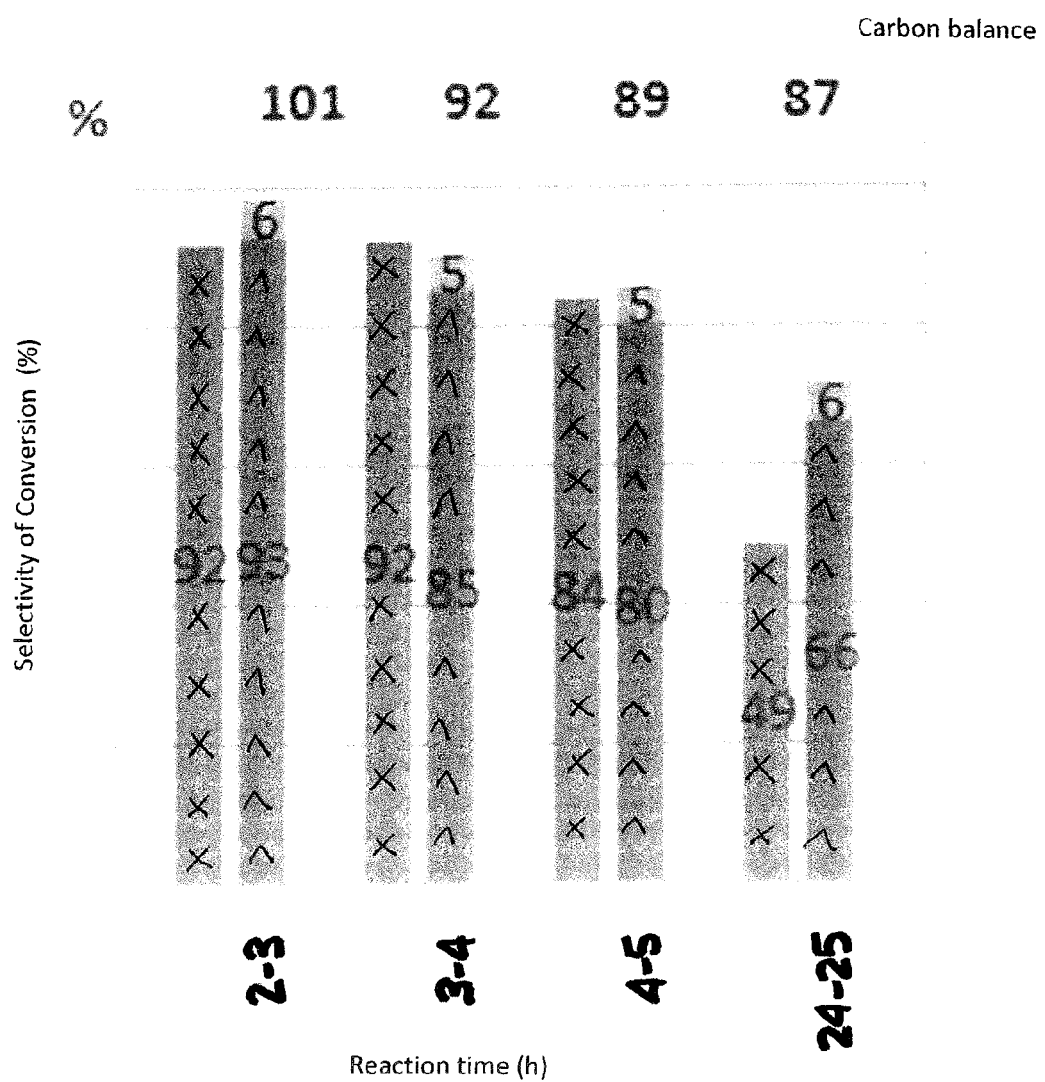
FIG. 2 is a diagram representing the conversion of the glycerol and the selectivity for acrolein as a function of the reaction time, observed over the catalyst 20 wt. % $H_4SiW_{12}O_{40}$/Q-10 operating in a fixed bed and forming the subject of example 1, which illustrates the disadvantages of the prior art.
Figure 3:
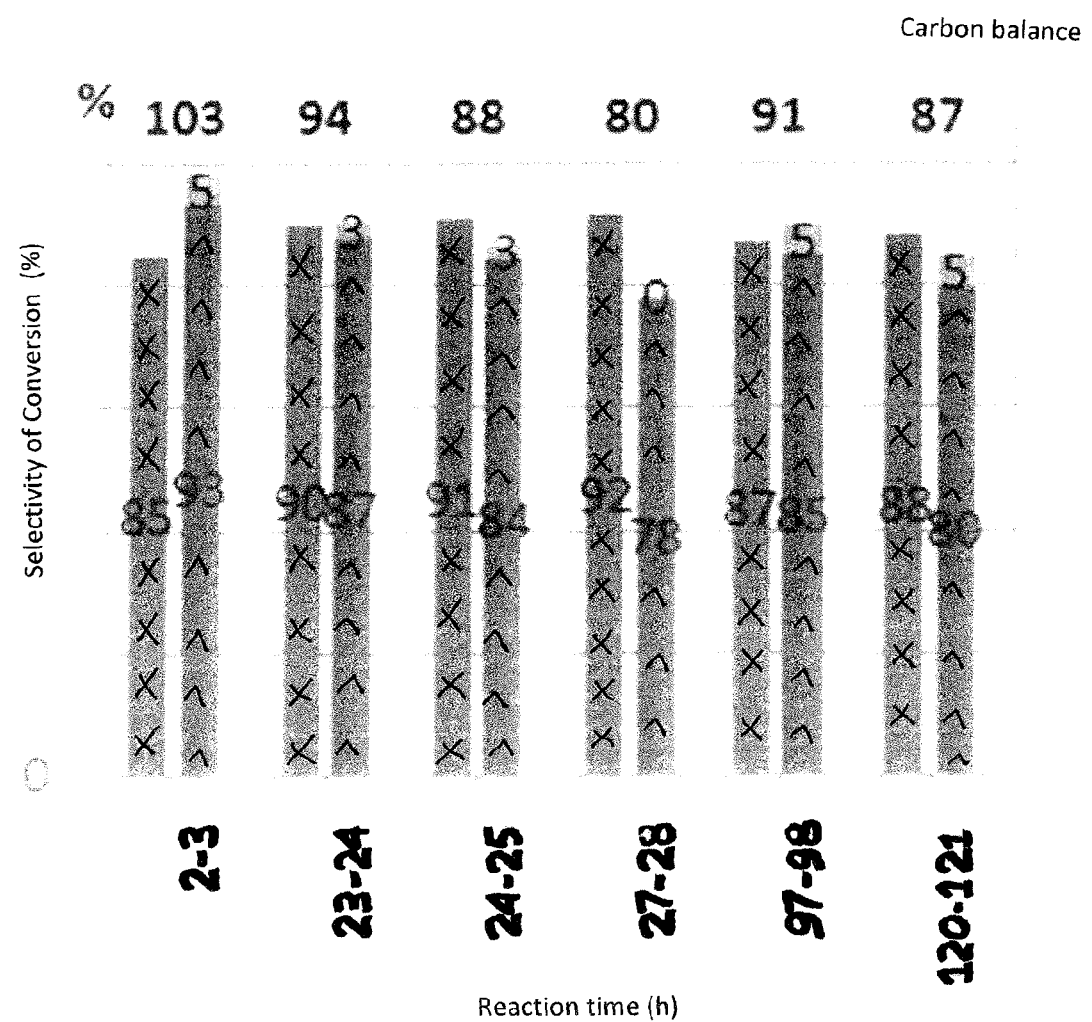
FIG. 3 is a diagram representing the conversion of the glycerol and the selectivity for acrolein as a function of the reaction time with alternating periodic regeneration over the catalyst 20 wt. % $H_4SiW_{12}O_{40}$/Q-10 operating in a fixed bed and forming the subject of example 1.

In FIGS. 2 and 3:
- ☒ represents the conversion of the glycerol (first columns)
- ◪ represents the selectivity for acrolein (second columns)
- ☐ represents the selectivity for acetol (columns above the second columns).

Figure 4:
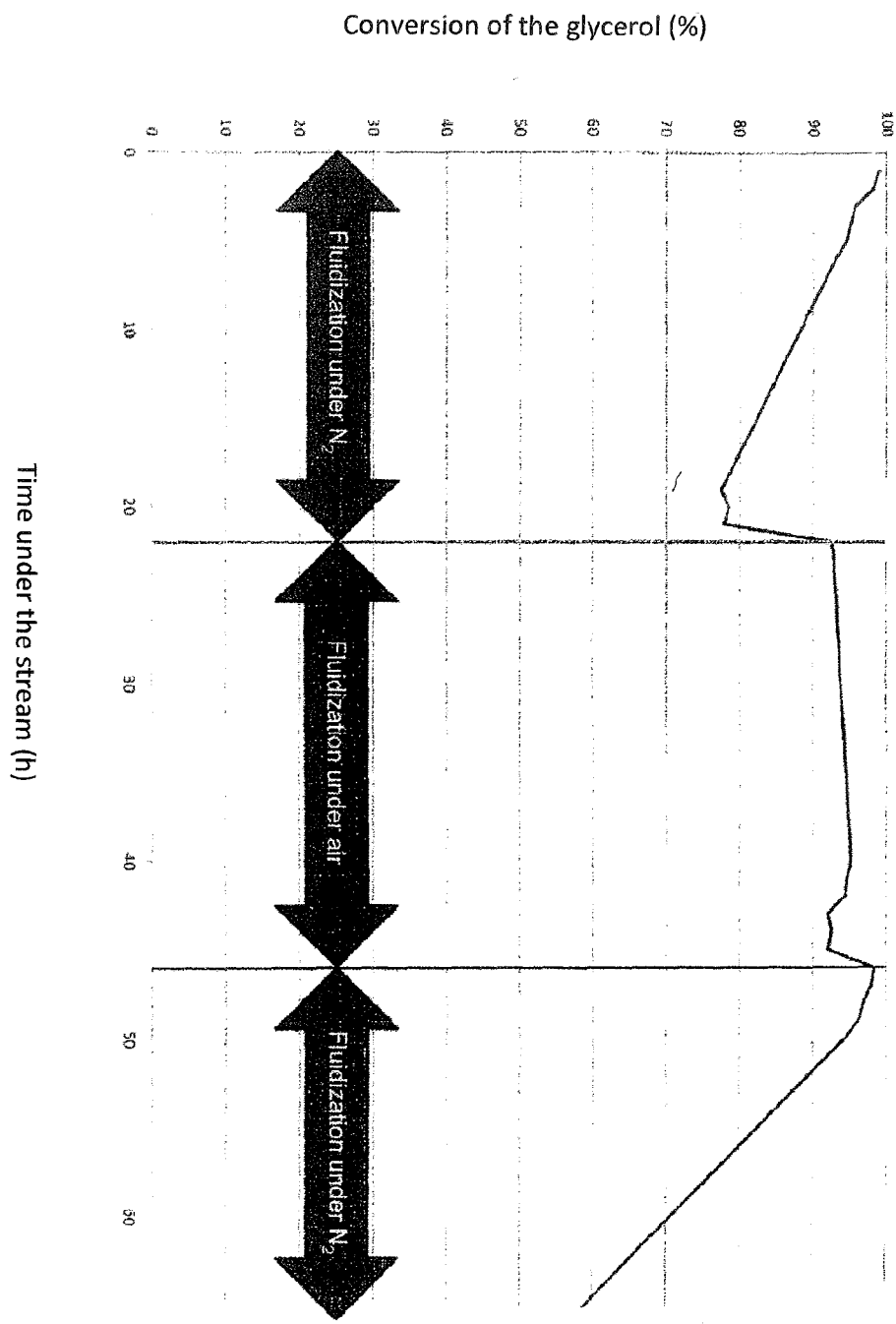

FIG. 4 is a diagram representing the change over time in the conversion of the glycerol in the same reactor, as a function of the fluidizing gas used.

Figure 1:
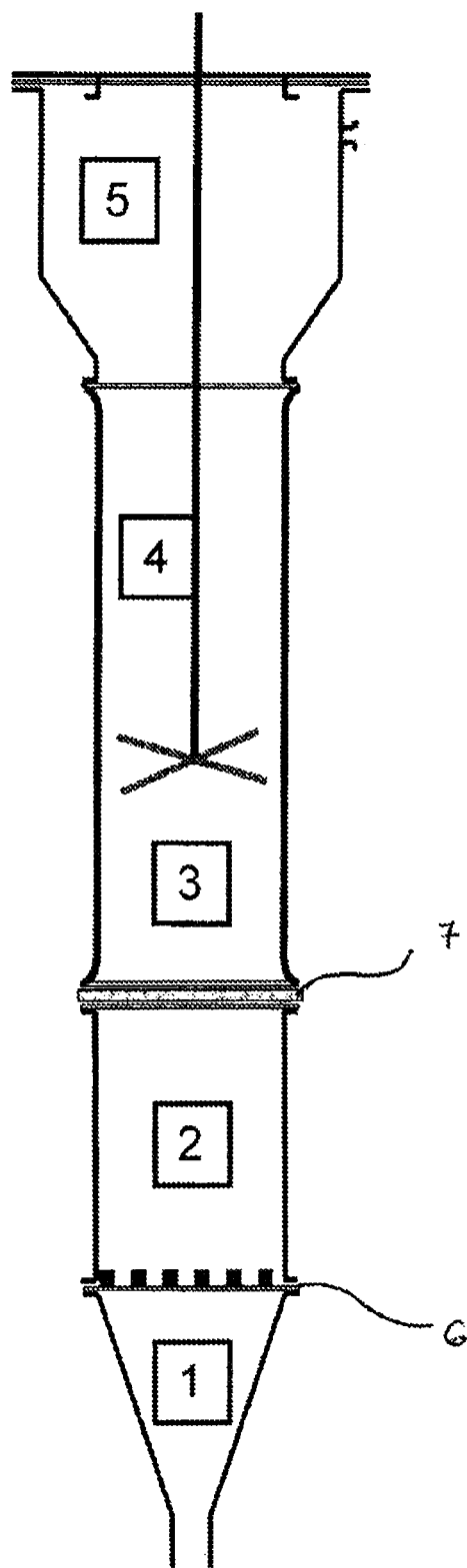
FIG. 1 represents the diagram of a fluidized bed reactor according to an alternative form of the invention and as used in example 2.

An example of a reactor which can be used to carry out the present invention is presented in FIG. 1. It is composed (from the bottom upwards) of a conical base 1 used to diffuse gas; of a first porous distributor 6 for the fluidizing gas; of a cylindrical part 2 containing a fluidizable or nonfluidizable solid, surrounded by a system for heating the gas, which can reach a temperature ranging up to 800° C.; of a second porous gas distributor 7; of a cylindrical reactor 3 comprising pressure and temperature sampling points, not represented, which can also act as system for the removal of gas; of a part 5 for release of the solid, making it possible to avoid the entrainment of the catalyst, followed by a cyclone which is used to recover the possible fine particles formed; and a system 4 for injection of the reaction mixture.

This system 4 slides vertically, so as to be able to adjust the height for injection into the fluidized bed and thus to create the two regions within the fluidized bed (region of acid catalysis and region of decoking the catalyst) at the desired point. The glycerol or glycerin solution is preferably injected after having been vaporized beforehand. The injection system has been designed so as to control the rate of flow of the fluid passing through it and thus optimize the gas/solid contact at its end.

EXAMPLE 1

Comparative

Catalytic Eehydration of Glycerol to Give Acrolein According to a Process of the Prior Art The reaction is first of all carried out in a fixed bed reactor with a heteropolyacid catalyst (diameter of the particles 221 μm, specific surface=218 m²/g) deposited on silica.

The catalyst is synthesized in the following way:

A reactor of autoclave type is filled with 20 ml of distilled water and 1.6 g of silica support of Cariact Q10 type (Fuji Silysia Chemical). After having closed the reactor, the stirring system is started and the temperature is set at 45° C. A solution of 0.4 g of $H_4SiW_{12}O_{40}$ dissolved in 5 ml of distilled water is added to the reactor at a rate of 1 ml/min using a dip pipe. After addition, the mixture is stirred for an additional 2 h before being transferred into a round-bottom flask in order to evaporate the solvent at 70° C. under vacuum using a rotary evaporator. The powder obtained is dried in an oven at 70° C. for 8 h.

The test catalytic reaction is carried out at 250° C. with 300 mg of catalyst placed in a fixed bed reactor made of stainless steel (15 mm in internal diameter, length of 120 mm) The reaction stream is composed of a 10% by weight aqueous glycerol solution fed via an HPLC pump at the rate of 1.5 ml/h. The solution is evaporated at 210° C. and diluted in helium (30 ml/min) before being introduced into the reactor. The reaction products are condensed in cold traps every hour during the first 5 hours under stream and then once again after reacting for 24 h. The duration of recovery of the products obtained in the trap is one hour. The condensed products are analyzed by HPLC. The results are presented in FIG. 2.

A significant decrease in the catalytic performance with the reaction time is observed. Thus, after 24 h under stream, the selectivity for acrolein and the conversion of the glycerol are both greatly reduced, 46% and 29% respectively, due to the significant coking at the surface of the catalyst.

Subsequently, the reaction is carried out by alternating a feed composed of a 10% by weight aqueous glycerol solution and a feed composed of air (7 Sml/min). The ratio of the durations of each phase is 1. The results obtained are presented in FIG. 3.

A rapid regeneration thus allows the catalyst to retain an excellent performance, 89% conversion on average and 85% selectivity on average, over a long period (120 h in this example).

EXAMPLE 2

Catalytic Dehydration of Glycerol to Give Acrolein According to the Invention

In one of the possible implementations of the present invention, the dimensions of the reactor are as follows:
- the conical part (1) of the reactor exhibits a bottom inlet for the gas with a diameter of 6.32 mm and a length of 20 mm. The total height of the conical part 1 is 85 mm with an internal diameter in its broadest part of 50 mm and in its narrowest part of 6.32 mm;
- the cylindrical part 2 used to heat the gas measures 255 mm in height and exhibits an internal diameter of 50 mm;
- in the same way, the body of the reactor 3 exhibits an internal diameter of 50 mm with a height of 700 mm;
- finally, the release part 5 measures 270 mm in height and has an internal diameter of 50 mm for the bottom part and of 90 mm for the top part.

The reaction products are recovered in a cold trap and are subsequently analyzed by HPLC. The noncondensable compounds are analyzed in line by mass spectrometry/gas chromatography.

EXAMPLE 3

Catalytic Dehydration of Glycerol to Give Acrolein According to the Invention 5 g of the catalyst of example 1 (diameter of the particles 221 μm, specific surface=218 m²/g), mixed with 76 g of silica support of Cariact Q10 type (Fuji Silysia Chemical) with a diameter of 293 μm, are placed in the reactor of example 2. The combined mixture is fluidized, either with a stream of molecular nitrogen or with a stream of air injected at a rate of 90 l/h (275° C., $P_{atm}$).

0.04 ml/min of a 20% by weight aqueous glycerol solution diluted with 5.5 l/h (275° C., $P_{atm}$) of molecular nitrogen is injected 3 cm above the distributor of the fluidizing gas. The fluidized bed is maintained at 275° C. and at atmospheric pressure.

In the first part of the experiment, the molecular nitrogen is used as fluidizing gas. FIG. 4 shows a gradual decrease in the conversion of the glycerol, from 98% initially to 78% after 21 h under the reaction stream. This deactivation phenomenon is related to the formation of coke at the surface of the catalyst, thus preventing access of the glycerol to the active acid sites. Subsequently, all other parameters furthermore remaining equal, the molecular nitrogen is replaced by air as fluidizing gas. The results show that the glycol conversion immediately goes back up to 92% and remains stable at this very high value for the following 25 h. When the system is again swung back to being placed under a stream of molecular nitrogen, the fall in the conversion is not immediate, which testifies to an effective regeneration of the catalyst by combustion of the coke formed at the surface of the catalyst. Obviously, in the absence of oxygen in the fluidized bed, the coking phenomenon again results in a gradual deactivation of the catalyst, as observed previously. The coking/regeneration cycles can be repeated without a detrimental change in the performance of the catalyst.

EXAMPLE 4

Catalytic Dehydration of Glycerol to Give Acrolein According to the Invention 5 g of the catalyst of example 1 (diameter of the particles 221 μm, specific surface=218 m$^2$/g), mixed with 76 g of silica support of Cariact Q10 type (Fuji Silysia Chemical) with a diameter of 293 μm, are placed in the reactor of example 2. The combined mixture is fluidized with a stream of molecular nitrogen injected at the rate of 90 l/h (275° C., $P_{atm}$). 0.04 ml/min of a 20% by weight aqueous glycerol solution diluted with 5.5 l/h (275° C., $P_{atma}$) of molecular nitrogen is injected over 2 h 3 cm above the distributor of the fluidizing gas. The fluidized bed is maintained at 275° C. and at atmospheric pressure. This pretreatment ensures the formation of a layer of coke at the surface of the catalyst. After halting the glycerol feed, a period of purging with molecular nitrogen is observed in order to discharge possible traces of glycerol remaining in the reactor. The molecular nitrogen is then replaced with air as fluidizing gas. The temperature is measured using three thermocouples placed in the bottom part, at the middle and in the top part of the fluidized bed reactor. Before changing over to air, the three temperatures are equal to 275° C.±2° C. Right from the injection of the air, a change in the temperature profile in the fluidized bed is noted. At their maxima, the temperatures recorded in the bottom part, at the middle and in the top part of the fluidized bed are 293° C., 278° C. and 279° C. respectively. These readings testify that the combustion of the coke, which is highly exothermic, takes place in the bottom part of the fluidized bed. After a few minutes, the three temperatures again become equal to the nominal value (i.e., 275° C.), testifying to the good uniformity of the fluidized bed and to the rapid combustion of the coke. This combustion is also confirmed by a $CO_2$ peak detected in the effluent stream from the reactor during this experiment (analysis carried out by mass spectrometry).

The invention claimed is:

1. A continuous process for the production of acrolein by catalytic dehydration of glycerol or glycerin in the presence of an acid catalyst in a fluidized bed reactor, said reactor comprising a lower region, for regeneration of the catalyst and an upper region for reaction of the glycerol or glycerin comprising the steps of introducing the glycerol or the glycerin into said upper region wherein the glycerol or glycerin is converted into acrolein by catalytic dehydration in the presence of the acid catalyst, and introducing an oxygen-comprising fluidized gas into said lower region, said oxygen-comprising fluidized gas being consumed in said lower region.

2. The process as claimed in claim 1, wherein the glycerol or the glycerin is introduced in the form of an aqueous solution in a concentration varying from 10% to 90% by weight.

3. The process as claimed in claim 2, wherein the glycerol or glycerin solution is introduced in a vaporized form.

4. The process as claimed in claim 1, wherein the acid catalyst is chosen from zeolites, phosphates, heteropolyacids, which are optionally supported and/or doped, catalysts of oxide or supported oxide types, or also of the type formed of zirconias, which are modified and/or doped.

5. The process as claimed in claim 4, wherein the catalyst is chosen from supported or unsupported heteropolyacids doped with at least one metal chosen from Cs, Rb, Ca, Fe, Zr, La, Hf and Bi.

6. The process as claimed in claim 1, wherein a dehydration temperature varies from 180 to 500° C.

7. The process as claimed in claim 1, wherein the fluidizing gas is chosen from air, $O_2$ and an $O_2/N_2$ mixture comprising up to 21 mol % of molecular oxygen.

8. The process as claimed in claim 1, wherein the fluidizing gas is heated to a temperature varying from 180 to 800° C.

9. The process as claimed in claim 8, wherein a pressure varies from atmospheric pressure to 10 bar.

10. The process as claimed in claim 1, wherein the upper region of the reactor comprises, from the bottom upwards, i) a part for introduction of the glycerol or glycerin, ii) a part for reaction by catalytic dehydration of the glycerol, and iii) a part for release of fine solid particles formed.

11. The process as claimed in claim 1, wherein the lower region of the reactor comprises, from the bottom upwards, a conical part for introduction of the fluidizing gas and a region for regeneration of the catalyst by the fluidizing gas.

* * * * *